(12) United States Patent
Schubert et al.

(10) Patent No.: US 10,101,265 B1
(45) Date of Patent: Oct. 16, 2018

(54) BIREFRINGENCE IMAGING CHROMATOGRAPHY BASED ON HIGHLY ORDERED 3D NANOSTRUCTURES

(71) Applicants: Mathias M. Schubert, Lincoln, NE (US); Tino Hofmann, Lincoln, NE (US); David S. Hage, Hickman, NE (US); Erika Pfaunmiller, Lincoln, NE (US); Craig M. Herzinger, Lincoln, NE (US); John A. Woollam, Lincoln, NE (US); Stefan Schoeche, Lincoln, NE (US)

(72) Inventors: Mathias M. Schubert, Lincoln, NE (US); Tino Hofmann, Lincoln, NE (US); David S. Hage, Hickman, NE (US); Erika Pfaunmiller, Lincoln, NE (US); Craig M. Herzinger, Lincoln, NE (US); John A. Woollam, Lincoln, NE (US); Stefan Schoeche, Lincoln, NE (US)

(73) Assignees: BOARD OF REGENTS FOR THE UNIVERSITY OF NEBRASKA, part interest; J.A. WOOLLAM CO., INC., part interest (*) Notice: Subject to any disclaimer, the term of this patent is extended or adjusted under 35 U.S.C. 154(b) by 372 days.

(21) Appl. No.: 14/756,345

(22) Filed: Aug. 31, 2015

Related U.S. Application Data

(60) Provisional application No. 62/123,119, filed on Nov. 7, 2014.

(51) Int. Cl.
  *G01N 21/21* (2006.01)
  *G01N 21/23* (2006.01)
  *G01J 4/04* (2006.01)

(52) U.S. Cl.
  CPC .............. *G01N 21/211* (2013.01); *G01J 4/04* (2013.01); *G01N 21/23* (2013.01)

(58) Field of Classification Search
  CPC ........ G01N 30/94; G01N 30/95; G01N 30/62; G01N 30/74; G01N 30/88; G01N 30/92; G01N 30/93; G01N 2030/945; G01N 2030/025; G01N 2030/027; G01N 2030/022; G01N 2030/743; G01N 2030/746; G01N 2030/8809; G01N 21/21;

(Continued)

(56) References Cited

U.S. PATENT DOCUMENTS 6,306,598 B1  10/2001  Charych et al.
6,468,759 B1  10/2002  Charych (Continued)

OTHER PUBLICATIONS

Kathleen Krause et al., "Pore analysis of obliquely deposited nanostructures by krypton gas adsorption at 87 K," 2011, Microporous and Mesoporous Materials, 143, pp. 166-173.

(Continued)

*Primary Examiner* — Gordon J Stock, Jr.
(74) *Attorney, Agent, or Firm* — James D. Welch

(57) ABSTRACT

Ellipsometers and polarimeters or the like to investigate analyte containing fluids applied to a substrate-stage having a multiplicity of nano-structures that project non-normal to a surface thereof, including dynamics of interaction therewith, to the end of evaluating and presenting at least partial Jones or Mueller Matricies corresponding to a multiplicity of locations over an imaged area.

47 Claims, 9 Drawing Sheets

(58) Field of Classification Search
CPC .............. G01N 21/211; G01N 21/213; G01N 2021/212; G01N 2021/213; G01N 2021/214; G01N 2021/215; G01N 2021/216; G01N 2021/217; G01N 21/23; G01J 4/00; G01J 4/02; G01J 4/04; G01J 2004/001; G01J 2004/002; G01J 2004/004; G01J 2004/005; G01J 2004/007; G01J 2004/008
See application file for complete search history.

(56) References Cited

U.S. PATENT DOCUMENTS

| | | | |
|---|---|---|---|
| 6,497,729 | B1 | 12/2002 | Moussy et al. |
| 6,628,369 | B2 | 9/2003 | Kumagai et al. |
| 7,300,031 | B2 | 11/2007 | Bertsch et al. |
| 7,341,841 | B2 | 3/2008 | Metzger et al. |
| 7,385,697 | B2 | 6/2008 | Woollam et al. |
| 7,432,371 | B2 | 10/2008 | Kriesel et al. |
| 7,589,242 | B2 | 9/2009 | French et al. |
| 7,598,094 | B2 | 10/2009 | Masters et al. |
| 7,611,908 | B2 | 11/2009 | Miller et al. |
| 7,615,381 | B2 | 11/2009 | Masters et al. |
| 7,629,137 | B2 | 12/2009 | Sauer-Budge et al. |
| 7,632,638 | B2 | 12/2009 | Sauer-Budge et al. |
| 7,648,844 | B2 | 1/2010 | Srivastava et al. |
| 7,749,445 | B2 | 7/2010 | Masters |
| 7,842,498 | B2 | 11/2010 | Um et al. |
| 7,897,406 | B2 | 3/2011 | Pinet et al. |
| 8,039,065 | B2 | 10/2011 | Ikeda et al. |
| 8,071,319 | B2 | 12/2011 | Metzger et al. |
| 8,859,230 | B2 | 10/2014 | Ramlav et al. |
| 8,871,444 | B2 | 10/2014 | Griffiths et al. |
| 8,908,180 | B2 | 12/2014 | Acher |
| 8,988,620 | B2 | 3/2015 | Israel et al. |
| 9,029,083 | B2 | 5/2015 | Griffiths et al. |
| 9,267,879 | B2* | 2/2016 | Ko ................... G01N 21/211 |
| 2003/0180966 | A1* | 9/2003 | Abbott ................... B82Y 30/00 436/518 |
| 2008/0259976 | A1* | 10/2008 | Hrudey ................ H01L 51/001 372/27 |
| 2010/0245820 | A1* | 9/2010 | Schubert ............... G01N 15/02 356/335 |
| 2014/0106980 | A1* | 4/2014 | Schubert ................ G01N 21/23 506/9 |
| 2015/0085365 | A1* | 3/2015 | Cadotte, Jr. .............. G02B 5/18 359/569 |

OTHER PUBLICATIONS

Edouard Bouvier et al., "Advances in size-exclusion separatipns of proteins and polymers by UHPLC," 2014, Trends in Analytical Chemistry, 63, pp. 85-94.
Thomas Walter et al., "Recent Innovations in UHPLC columns and instrumentation," 2014, Trends in Analytical Chemistry, 63, pp. 14-20.
Szabolcs Fekete et al., "Current and future trends in UHPLC," 2014, Trends in Analytical Chemistry, 63, pp. 2-13.
Xue Wang et al., "Microfluidics-to-mass spectrometry: A review of coupling methods and applications," 2015, Journal of Chromatography A, 1382, pp. 98-116.
Jean-Luc Wolfender et al., "Current approaches and challenges for the metabolite profiling of complex natural extracts," 2015, Journal of Chromatography A, 1382, pp. 136-164.
K. Broeckhoven et al., "The future of UHPLC: Towards higher pressure and/or smaller particles?," 2014, Trends in Analytical Chemistry, 63, pp. 65-75.
H.E. Hauck et al., "Ultra Thin-Layer Chromatography," 2003, Chromatographia Supplement, vol. 57, S-313-S-315.
Colin F. Poole, "Thin-layer chromatography: challenges and opportunities," 2003, Journal of Chromatography A, 1000, pp. 963-984.
Louis W. Bezuidenhout et al., "Ultrathin layer chromatography on nanostructured thin films," 2008, Journal of Chromatography A, 1183, pp. 179-185.
A. J. Oko et al., "Time resolved chromatograms in ultra-thin layer chromatography," 2012, Journal of Chromatography A, 1249, pp. 226-232.
A.J. Oko et al., "Analyte migration in anisotropic nanostructured ultrathin-layer chromatography media," 2011, Journal of Chromatography A, 1218, pp. 2661-2667.
Salwa K. Poole et al., "High performance stationary phases for planar chromatography," 2011, Journal of Chromatography A, 1218, pp. 2648-2660.
Gertrud E. Morlock, "Miniaturized planar chromatography using office peripherals—Office chromatography," 2015, Journal of Chromatography A, 1382, pp. 87-96.
Jing Chen et al., "On-Chip Ultra-Thin Layer Chromatography and Surface Enhanced Raman Spectroscopy," 2012, Lab on a Chip, 12, pp. 3096-3102.
Hawkeye et al., "Glancing angle deposition: Fabrication, properties, and applications of micro- and nanostructured thin films," 2007, JVSTA, 25, pp. 1317-1325.
K. Robbie et al., "Sculptured thin films and glancing angle deposition: Growth mechanics and applications," 1997, JVSTA, 15, pp. 1460-1465.
Joseph Sherma, "Review of Advances in the thin layer chromatography of pesticides: 2006-2008," 2009, Journal of Environmental Science and Health Part B, 44, pp. 193-203.
Heinz E. Hauck et al., "Ultrathin-Layer Chromatography," 2002, Journal of Chromatographic Science, vol. 40, pp. 1-3.
Lukasz Ciesla et al., "Two-dimensional thin-layer chromatography in the analysis of secondary plant metabolites," 2009, Journal of Chromatography A, 1216, pp. 1035-1052.
Jonathan E. Clark et al., "Technique for Ultrathin Layer Chromatography Using an Electrospun, Nanofibrous Stationary Phase," 2009, Analytical Chemistry, 81, pp. 4121-4129.
Gertrud E. Morlock et al., "Miniaturized Planar Chromatography Using Office Peripherals," 2010, Analytical Chemistry, 82, pp. 2940-2946.
S.R. Jim et al., "Engineered Anisotropic Microstructures for Ultrathin-Layer Chromatography," 2010, Analytical Chemistry, vol. 82, No. 12, pp. 5349-5356.

* cited by examiner

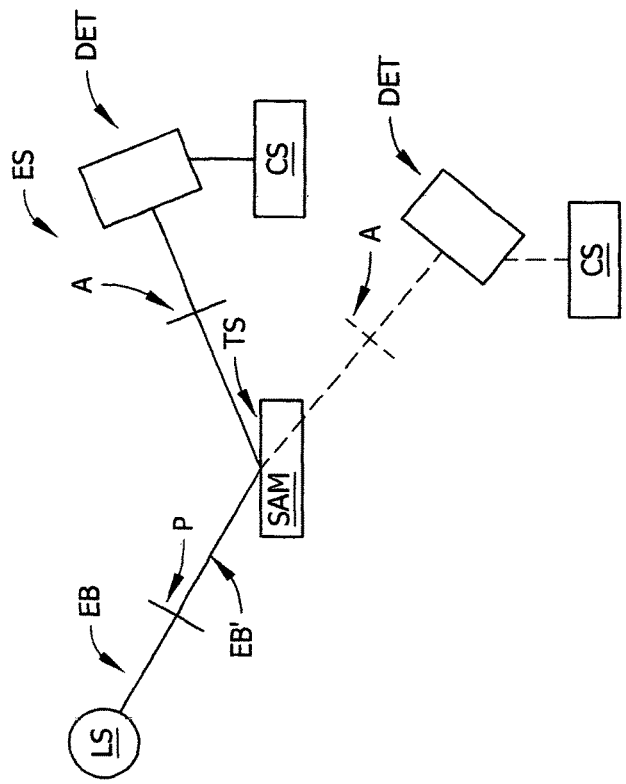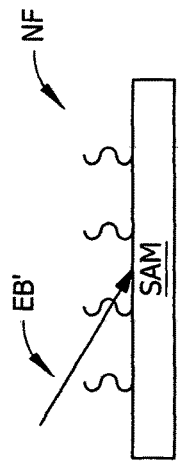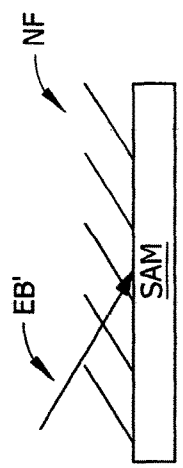

| $M_{14}$ | $M_{24}$ | $M_{34}$ | $M_{44}$ |
|---|---|---|---|
| $M_{13}$ | $M_{23}$ | $M_{33}$ | $M_{43}$ |
| $M_{12}$ | $M_{22}$ | $M_{32}$ | $M_{42}$ |
| $M_{11}$ | $M_{21}$ | $M_{31}$ | $M_{41}$ |

FIG. 4b

| $J_{13}$ | $J_{23}$ | $J_{33}$ |
|---|---|---|
| $J_{12}$ | $J_{22}$ | $J_{32}$ |
| $J_{11}$ | $J_{21}$ | $J_{31}$ |

FIG. 4a $$\begin{bmatrix} S_0 \\ S_1 \\ S_2 \\ S_3 \end{bmatrix}_{out} = \begin{pmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{pmatrix} \begin{bmatrix} I_P + I_S \\ I_P - I_S \\ I_{45} - I_{-45} \\ I_{RC} - I_{LC} \end{bmatrix}_{in}$$

BIREFRINGENCE IMAGING CHROMATOGRAPHY BASED ON HIGHLY ORDERED 3D NANOSTRUCTURES

This Application claims benefit of Provisional 62/123,119 Filed Nov. 7, 2014, which is incorporated by reference hereinto.

TECHNICAL FIELD

The present invention relates to chromatography, and more particularly to application of ellipsometers and polarimeters or the like to investigate analyte containing fluids applied to a substrate-stage comprising a multiplicity of nano-structures that project non-normal to a surface thereof, including dynamics of interaction therewith, to the end of evaluating and presenting at least partial Jones or Mueller matrices that correspond to investigated locations over an imaged area.

BACKGROUND

The areas of Ellipsometry and Chromatography are both well developed. Ellipsometry involves causing a beam of electromagnetic radiation which is in a known polarization state to interact with a sample in a way that changes the polarization state thereof, and then applying mathematical regression to data pertaining to said change. Ellipsometric Parameters such as well known PSI ($\psi$) and DELTA ($\Delta$) are typically determined by said procedure. Imaging ellipsometers are also known, and enable investigating samples over an area region thereof rather than at simply one small point. For instance, PSI ($\psi$) and DELTA ($\Delta$) values for a multiplicity of points over an area of said sample can be determined and shown in a two, (or more), dimensions.

Chromatography is a technique for separation of analytes in mixtures of analytes present in a mobile phase, by interaction with a stationary phase. Various analyte constituents present in a mixture travel at different speeds, therefore enabling subtle differences in what is termed a "partition coefficient" with which each analyte presents to result in a different spatial distribution for each. Chromatography can be preparative, wherein the purpose is analyte separation for purification purposes, or it can be analytical which is focused on providing information on relative amounts of various analytes present and/or determining how various analytes move through a stationary phase over time. The latter application is more associated with the presently Claimed invention. In particular the present invention is properly thought of as primarily a version of planar chromatography in which the stationary phase is not merely, a flat paper or the like, but rather comprises a multiplicity of nano-structures that project non-normal to a surface thereof.

A Computer Search for Patents that combine Ellipsometer and Chromatography with an eye to providing images of various Jones or Mueller Matrix Elements for an area on a sample, returned one hit, a Patent to Frence, et al., U.S. Pat. No. 7,589,242. A similar search for Jones Matrix and Imaging Ellipsometer returned two Hits, a Patent to Woollam et al. U.S. Pat. No. 7,385,697 and a Patent to Acher, U.S. Pat. No. 8,908,180. Importantly, a Computer Search for Mueller Matrix and Chromatography returned no hits.

A known paper is titled "Imaging Ellipsometry of Graphene", by Wurstbauer et al., Appl. Physics Lett., 97, 231901, 2010.

The present invention will be understood by reference to the following Specification.

DISCLOSURE OF THE INVENTION

The present invention applies highly ordered 3-dimensional nanostructured ultra-thin layers (3DN-UTL's) as stationary phases for the chromatographic separation of, and simultaneous ultrasensitive detection of separating target analytes and other sample constituents, by monitoring birefringence imaging in transmission or reflection modes, via obtaining spectroscopic ellipsometry measurement images observed in diagonal, or off-diagonal Jones or Mueller matrix element images. The present invention applies 3DN-UTL's to effect 2- and 3-dimensional chromatography utilizing anisotropic flow and interaction profiles.

Separation, of target analytes and other sample constituents achieved by applying said stationary phases that are composed of said ultra-thin layers of highly ordered nano-structures can be influenced by varying geometry and composition of synthesised, self-organizing and scalable nanostructures that are fabricated by controlling flux direction with respect to a substrate normal, during deposition thereof.

Said synthesised, self-organizing and scalable nanostructures in ultra-thin layer chromatography (3DN-UTLC) are applied in combination with imaging spectroscopic ellipsometry readout principles to enable determination of analyte volume within the nanostructure support, without the need for additional chemical labels for optical (eg. fluorescence), detection. Information on the strength of interaction between a target analyte and a stationary phase, and the rate of travel of the target analyte, are obtained by a time-resolved ellipsometric readout. Further, the shape of the 3DN-UTLC nanostructures can be engineered to induce 2- and 3-dimensional solvent flow profiles that lead to 2- and 3-dimensional analyte(s) and other sample constituents solvent flow profiles that lead to 2- and 3-dimensional separations.

The present invention utilizes an optical detection mechanism which is based on birefringence changes caused by the dielectric screening of the nanostructures by an analyte. The detection mechanism suppresses false read-outs because only analyte in the vicinity of the nanostructures is able to screen their dielectric response. Thus, the present invention provides for real time readout of travel and separation of analyte(s) and other sample constituents without the necessity of using chemical labels. Said ellipsometric birefringence effects of 3DN-UTLC can be achieved over a wide spectral range from THz to the UV spectrum thereby enabling free chemical specimen identification based on optical "fingerprints".

The present invention can also be applied to determine the nano-fluidic properties of 3DN-UTL's which can be detected by imaging and varying particle flux direction with respect to a substrate surface normal, thereby engineering the 3-dimensional shape of the nanostructures.

The present invention is an imaging ellipsometer or polarimeter system capable of producing at least partial Jones or Mueller matrices corresponding to a multiplicity of locations over an image area, comprising:

a) a source of a beam of electromagnetic radiation;
b) a polarization state generator;
c) a substrate-stage comprising a multiplicity of nano-structures that project non-normal to a surface thereof;
d) a polarization state analyzer; and
e) a data detector.

It is to be understood that said imaging ellipsometer or polarimeter system presents with inherent p- and s-coordinates, and that in use a fluid selected from the group consisting of:
 a liquid; and
 a gas;
which optionally contains one or more analytes, is entered to said substrate-stage nanostructures which, over time can migrate therewithin while a beam of electromagnetic radiation from the source thereof is caused to have a polarization state imposed thereupon by the polarization state generator, then interact with said substrate-stage over an imaged area thereof, proceed through said polarization state analyzer and enter said data detector, and wherein said data detector provides output data corresponding to a multiplicity of points over said area of said substrate-stage being imaged. Said output data is sufficient to enable production of said at least partial Jones or Mueller matrices that correspond to a multiplicity of locations over said imaged area.

The imaging ellipsometer or polarimeter system can have a substrate-stage which is rotatable about a perpendicular to said surface, and wherein the beam of electromagnetic radiation approaches the surface of said substrate-stage along a substantial perpendicular thereto, then transmits therethough, passes through said polarization state analyzer, and enters said data detector. Again, data acquired can be applied to produce elements of said at least partial Jones or Mueller matrix that present with image information in diagonal or off-diagonal elements thereof, effected by rotating said substrate-stage about said perpendicular to said surface thereof to provide alignment of said nano-structures with said ellipsometer or polarimeter system p- or s-coordinates, or at a rotation angle therebetween, respectively. The effects of isotropic properties of said substrate-stage can be included along with anisotropic properties introduced by the presence of said nanostructures, in the data produced by the data detector, and thus appear in the elements of said at least partial Jones or Mueller matrix image information in diagonal or off-diagonal elements thereof, respectively.

Further, the imaging ellipsometer or polarimeter system can involve said substrate-stage being rotatable about a perpendicular to said surface, and wherein the beam of electromagnetic radiation approaches the surface of said substrate-stage along a non-perpendicular thereto such that a plane of incidence is defined, then reflects therefrom, passes through said polarization state analyzer and enters said data detector, data from which can be applied to produce elements of said at least partial Jones or Mueller matrix that present with image information in diagonal or off-diagonal elements thereof effected by rotating said substrate-stage about said perpendicular to said surface thereof, to provide alignment of said nano-structures with said ellipsometer or polarimeter system p- or s-coordinates, or at a rotation angle therebetween, respectively. Said imaging ellipsometer or polarimeter system can involve setting a preferred rotation angle of said substrate-stage that provides said plane of incidence is at an angle to the direction in which said non-normal nanostructures are caused to project within said said ellipsometer or polarimeter system p- and s-coordinate system.

The imaging ellipsometer or polarimeter system can involve the non-normal nanostructures of said substrate-stage are formed by glancing angle deposition thereof onto said surface.

The imaging ellipsometer or polarimeter system can involve the source of electromagnetic radiation provides wavelengths in a THZ to UV spectral range.

Said imaging ellipsometer or polarimeter system can involve the polarization state generator and polarization state analyzer are each fixed polarizers, before and after the substrate-stage, respectively, and in which each said fixed polarizer can be aligned relative to the nanostructure orientation such that data detector sensitivity to anisotropic properties of said nanostructures is enhanced in the vicinity of optionally present analytes. The imaging ellipsometer or polarimeter system can involve the two fixed polarizers are crossed, so as to enable detection of Jones or Mueller matrix off-diagonal elements that provide insight to said anisotropic properties.

The imaging ellipsometer or polarimeter system can involve said substrate-stage being contained within a substantially enclosed cell which comprises windows through which said of electromagnetic radiation enters and exits. Further, said windows can be oriented so that said beam of electromagnetic radiation enters and exits perpendicular thereto.

The imaging ellipsometer or polarimeter system can be oriented such that the substrate-stage is oriented such that the electromagnetic beam directly encounters said nanostructures.

The imaging ellipsometer or polarimeter system can involve the substrate-stage being oriented such that the electromagnetic beam passes through the surface before encountering said nanostructures.

The imaging ellipsometer or polarimeter system can be oriented so that said beam of electromagnetic radiation is caused to approach the substrate-stage along a substantial perpendicular to the surface thereof, while the nanostructures are oriented to project in a desired direction, such that the p- and s-coordinates of said imaging ellipsometer or polarimeter system can be calibrated thereto.

A present invention method of monitoring the interaction of a fluid with a substrate comprises the steps of:
 a) providing a system capable of determining and imaging elements of an at least partial Jones, or at least partial Mueller matrix for each of a multiplicity of positions over an imaged area of a substrate;
 b) providing a substrate that comprises nanostructures that project from a substantially planar substrate surface non-normal thereto;
 c) entering a fluid selected from the group consisting of:
  a liquid, and
  a gas;
 to said substrate nanostructures;
 d) applying said provided system to determine and provide an observable image that provides insight to anisotropic properties of said substrate-fluid combination for at least one element of said determined at least partial Jones or Mueller matrix corresponding to said imaged area of said substrate.

Said method can provide that the provided system is an imaging ellipsometer or polarimeter, for instance comprising:
 a) a source of a beam of electromagnetic radiation;
 b) a polarization state generator;
 c) a substrate-stage comprising a multiplicity of nanostructures that project non-normal to a surface thereof, said substrate-stage being rotatable about a perpendicular to said surface;
 d) a polarization state analyzer; and
 e) a data detector;
said imaging ellipsometer or polarimeter presenting system inherent p- and s-coordinates;
such that in use a fluid selected from the group consisting of:

a liquid; and a gas;

which optionally contains one or more analytes is entered to said substrate-stage nanostructures which, over time can migrate therewithin while a beam of electromagnetic radiation from the source thereof is caused to have a polarization state imposed thereupon by the polarization state generator, then interact with said substrate-stage over an imaged area thereof, proceed through said polarization state analyzer and enter said data detector, and wherein said data detector provides output data corresponding to a multiplicity of points over said area of said substrate-stage being imaged, which output data is sufficient to enable production of said at least partial Jones or Mueller Matrices that correspond to a multiplicity of locations over said imaged area.

Said method can involve the beam of electromagnetic radiation is directed to approach the surface of said substrate along a substantial perpendicular thereto, then transmits therethough, passes through said polarization state analyzer, and enters said data detector, data from which can be applied to produce elements of said at least partial Jones or Mueller matrix that present with image information in diagonal or off-diagonal elements thereof effected by rotating said substrate about said perpendicular to said surface thereof to provide alignment of said nano-structures with said ellipsometer or polarimeter system p- or s-coordinates, or at a rotation angle therebetween, respectively, and the effects of isotropic properties of said substrate can included along with anisotropic properties introduced by the presence of said nanostructures, in the data produced by the data detector, and thus appear in the elements of said at least partial Jones or Mueller matrix image information in diagonal or off-diagonal elements thereof.

The method can involve the beam of electromagnetic radiation being directed to approach the surface of said substrate along a non-perpendicular thereto such that a plane of incidence is defined, then reflects therefrom, passes through said polarization state analyzer and enters said data detector, data from which can be applied to produce elements of said at least partial Jones or Mueller Matrix that present with image information in diagonal or off-diagonal elements thereof effected by rotating said substrate about said perpendicular to said surface thereof, to provide alignment of said nano-structures with said ellipsometer or polarimeter system p- or s-coordinates, or at a rotation angle therebetween, respectively.

The method can involve a preferred rotation angle of said substrate provides such that said plane of incidence is at an angle to the direction in which said non-normal nanostructures are caused to project within said said ellipsometer or polarimeter system p- and s-coordinate system.

The method can involve the non-normal nanostructures of said substrate being formed by glancing angle deposition thereof onto said surface.

The method can involve the source of electromagnetic radiation provides wavelengths in a THZ to UV spectral range.

The method can involve that the polarization state generator and polarizations state analyzer are each fixed polarizers, before and after the substrate, respectively, and in which each said fixed polarizer is aligned relative to the nanostructure orientation such that data detector sensitivity to anisotropic properties of a fluid entered into said nanostructures is enhanced.

The method can involve the two fixed polarizers being crossed so as to enable detection of Jones or Mueller Matrix off-diagonal elements that provide insight to said anisotropic properties.

The method can involve said substrate being contained within a substantially enclosed cell which comprises windows through which said of electromagnetic radiation enters and exits, and can involve said windows being oriented so that said beam of electromagnetic radiation enters and exits perpendicular thereto.

The method can involve the substrate being oriented such that the electromagnetic beam directly encounters said nanostructures.

The method can involve the substrate being oriented such that the electromagnetic beam passes through the surface before encountering said nanostructures.

The method can involve said beam of electromagnetic radiation being caused to approach the substrate along a substantial perpendicular to the surface thereof, while the nanostructures are oriented to project in a desired direction, such that the p- and s-coordinates of said imaging ellipsometer or polarimeter system can be calibrated thereto.

The method can involve that the properties of said substrate-fluid combination for at least one element of said determined at least partial Jones or Mueller matrix corresponding to said imaged area of said substrate are determined by obtaining multiple data sets that correspond to multiple orientations of said substrate-fluid combination and performing a simultaneous regression thereonto to provide information regarding anisotropy.

The method can involve the properties of said substrate-fluid combination for at least one element of said determined at least partial Jones or Mueller matrix corresponding to said imaged area of said substrate being determined and observed over time to capture the dynamics of a process.

The method can involve the properties of said substrate for at least one element of said determined at least partial Jones or Mueller matrix corresponding to said imaged area of said substrate being determined in a first step, followed by introduction of a fluid to said nanostructures and the properties of said substrate-fluid combination for at least one element of said determined at least partial Jones or Mueller matrix corresponding to said imaged area of said substrate is then determined in a second step. The difference between the results obtained in said first and second steps can then be analyzed.

Said method can involve that the results determined are applied to determine analyte type present in said fluid.

Further, the method can involve that the results determined provide insight into travel and separation of analyte constituents over a period of time after the containing fluid is entered to said nanostructures.

And said method can be applied to provide insight into travel and separation of analyte constituents over a period of time after the containing fluid is entered to said nanostructures and therefore strength of interaction.

The method can be applied to provide insight into volume within the nanostructures.

The method can be applied to provide real time results.

The method can be applied with the nanostructure geometry engineered to emphasise nano-fluidic properties of the nanostructures in relation to their shape.

The method can be applied with the nanostructure geometry engineered to create an anisotropic solvent flow profile, and that can involve solvent flow profiles in one, two or three dimensions.

A present invention imaging ellipsometer or polarimeter per se., or the methodology of application, can involve that said surface said multiplicity of nano-structures that project non-normal to is substantially planar, or is other than substantially planar.

And an imaging ellipsometer or polarimeter system per se., or the methodology of application, can involve that the preferred rotation angle of said substrate-stage provides that said plane of incidence is at an essentially 45 degree angle to the direction in which said non-normal nanostructures are caused to project within said ellipsometer or polarimeter system p- and s-coordinate system. Of course said plane of incidence can be set to any angle between 0.0-90 degrees.

The present invention will be better understood by reference to the Detailed Description Section of this Specification, with reference to the Drawings.

BRIEF DESCRIPTION OF THE DRAWINGS

FIG. 1 shows an ellipsometer system that presents an electromagnetic beam to a sample substantially along a normal to a surface thereof to investigate the sample in a transmission mode.

FIG. 2 shows an ellipsometer system that presents an electromagnetic beam to a sample substantially along an oblique angle to a surface thereof, both in reflection and transmission modes.

FIGS. 3a and 3b show two examples of Samples (SAM) comprising substantially straight Nano-Fibers (NF) that project other than perpendicular to a Sample Surface, and Nano-Fibers (NF) that are non-straight.

FIGS. 4a and 4b show basic Jones and Mueller matrices.

FIG. 5a shows a mathematical representation of a Mueller Matrix.

FIG. 5b shows a diagram of an electromagnetic beam in an ellipsometer system, indicating the Plane and Angle of Incidence, and the "p" and "s" components of the Incident and Reflected Beams as indicated in FIG. 5a.

FIG. 6aA shows that many "N's" are present on a large substrate that has a dimension on the order of 10's of millimeters.

FIG. 6aB focuses on one of the "N's" in FIG. 6aA, showing nano-fibers, (100's of microns long), being oriented at a slant.

FIG. 6aC shows that there are nano-fibers present in the region of the "N" in FIG. 6aB that project non-normal to the surface of said FIG. 6aB sample, and are of a dimension on the order of 100's of nanometers.

DETAILED DESCRIPTION

Turning now to the Drawings, FIG. 1 shows an ellipsometer system (ES) that presents a Source (LS) of an Electromagnetic Beam (EB) to a Sample (SAM) substantially along a normal to a surface thereof, said Electromagnetic Beam (EB) to investigate the Sample (SAM) in a transmission mode. Shown are a Source of Electromagnetic Radiation (LS), a Polarizer (P), the investigated Sample (SAM), an Analyzer (A) and Detector (DET). Also shown is a Computer System that in use analyzes Data provided by the Detector (DET) and provides Jones or Mueller matrix elements.

FIG. 2 shows an Ellipsometer system (ES) much like that in FIG. 1, except that it presents an Electromagnetic Beam (ES) to a Sample (SAM) substantially along an oblique angle to a surface thereof, both in reflection and transmission modes. Again shown are a Source (LS) of Electromagnetic Radiation (EB), a Polarizer (P), the investigated Sample (SAM), an Analyzer (A) and Detector (DET). Also shown is a Computer System that in use analyzes Data provided by the Detector (DET) and provides Jones or Mueller matrix elements.

FIGS. 3a and 3b show two examples of Samples (SAM) comprising substantially straight Nano-Fibers (NF) that project other than perpendicular to a Top Sample Surface (TS), and Nano-Fibers (NF) that are non-straight. The FIG. 3a Nano-Fibers (NF) can be formed by deposition thereof at an angle to the Top Surface (TS) of a Sample (SAM) by a "shadowing technique", and the FIG. 3b Nano-Fibers (NF) can be formed by deposition thereof while the Sample (SAM) is being rotated. Samples utilized in the present invention comprise such Nano-Fibers (NF) as a means to induce anisotropy, which in turn causes signals to appear in Off-Diagonal Matrix Elements. It is to be noted that said FIGS. 3a and 3b show a Beam of Electromagnetic Radiation (EB') interacting with the Nano-Fibers (NF) and Sample (SAM). This should be interpreted in view of FIGS. 1 and 2, where Beam (EB') is Beam (EB) after it passes through the Polarizer (P) shown therein. FIGS. 3a and 3b should be considered as views of very relevant expanded Samples (SAM) in FIGS. 1 and 2.

FIGS. 4a and 4b show Jones and Mueller matrices. Note that in practice the first Element J11 or M11 is typically determined but not displayed. Instead each of the remaining Elements are divided thereby. In what Figures that follow, the same matrix Element Numbering is applied.

Figures 5A, 5B:
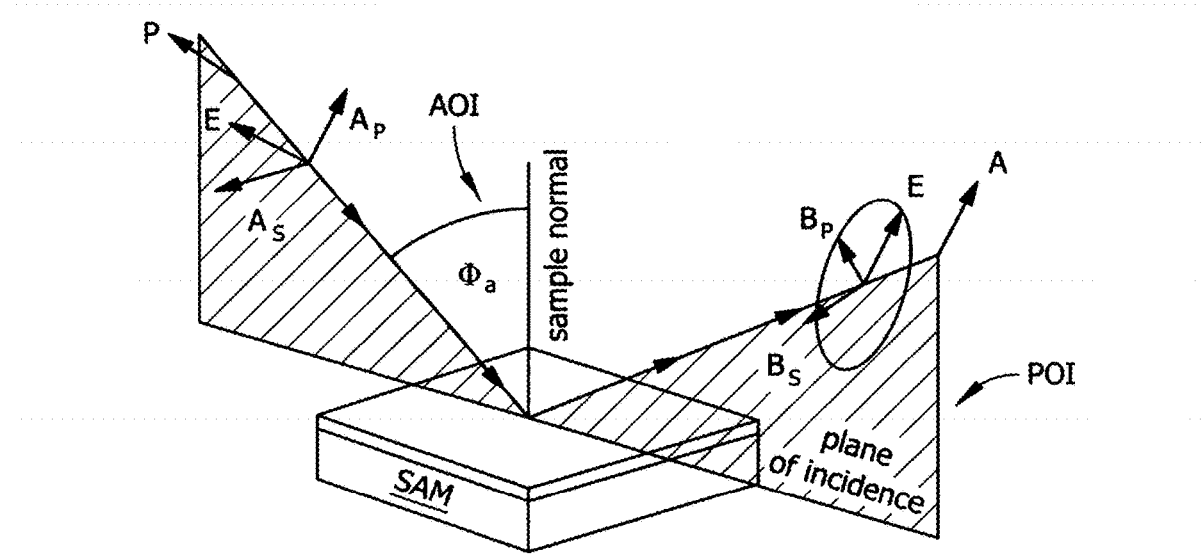

FIG. 5a shows a mathematical representation of a Mueller Matrix applied to transform an Input Vector to an Output Vector.

FIG. 5b shows a diagram of an electromagnetic beam in an ellipsometer system, indicating the Plane (POI) and Angle (AOI) of Incidence, and the "p" and "s" components of the Incident and Reflected Beams as indicated in FIG. 5a. Indications of the Polarizer (P) and Analyzer (A) are also shown. "E" indicates the direction of the Electric Filed at said Polarizer (P) and Analyzer (AP).

Figure 6A:
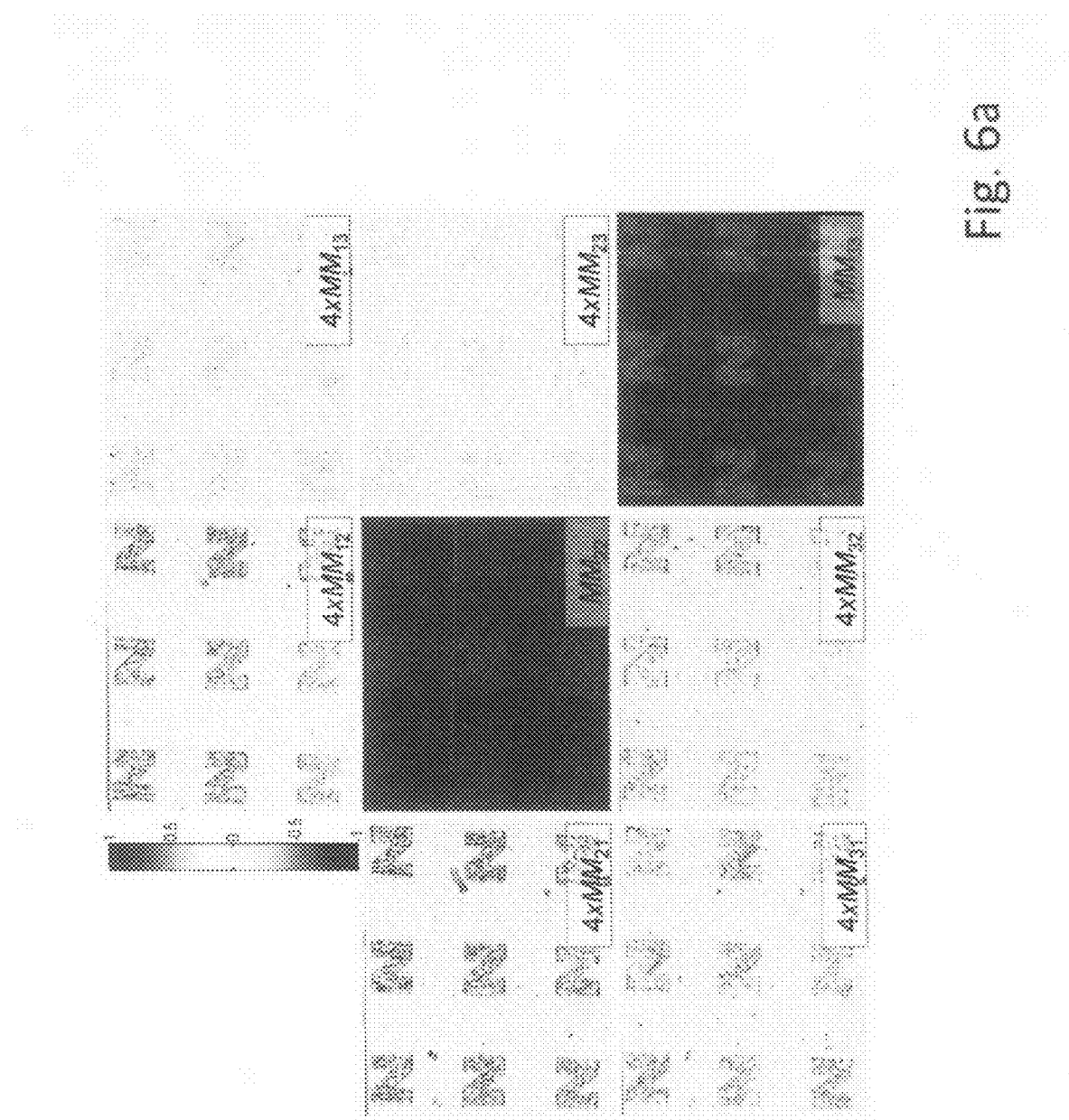
FIG. 6a shows how different elements of a Mueller Matrix demonstrate different images of the same sample that comprises patterned "N's" when investigated in transmission.

FIG. 6a shows how different elements of a Mueller matrix demonstrate different images of the same portion of a sample with dimensions of 300×300 microns. Patterned "N's" made of 500 nm of Si STF on glass are shown as investigated in transmission using a system as shown in FIG. 1. Note that the Sample (SAM) surface has "shadowed" Nano-Fibers (NF) on the Surface thereof as exemplified in FIG. 3a, in the areas that appear as "N's". FIGS. 6aA, 6aB and 6aC are included to give better insight as to what is being shown in FIG. 6a. FIG. 6aA shows that many "N's" are present on a large substrate that has a dimension on the order of 10's of millimeters. FIG. 6aB focuses in on one of the "N's" having a dimension of 100's of microns, and FIG. 6aC shows that there are nano-fibers present in the region of the "N" in FIG. 6aB. These nano-fibers are projected non-normal to the surface, (ie. at a slant), as in said FIG. 6a and are of a dimension on the order of 100's of nanometers. Note that the various Mueller matrix Elements shown provide differing image results of the same sample being investigated.

Figure 6A:
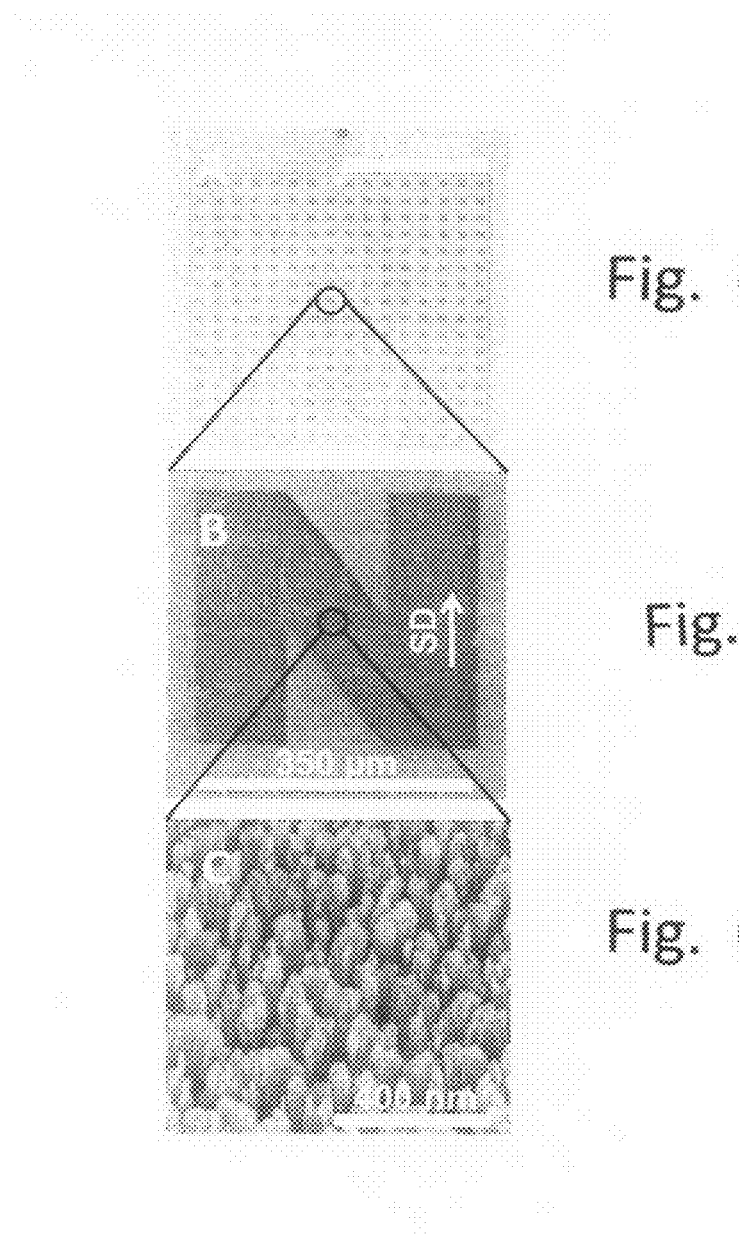
Figure 6B:
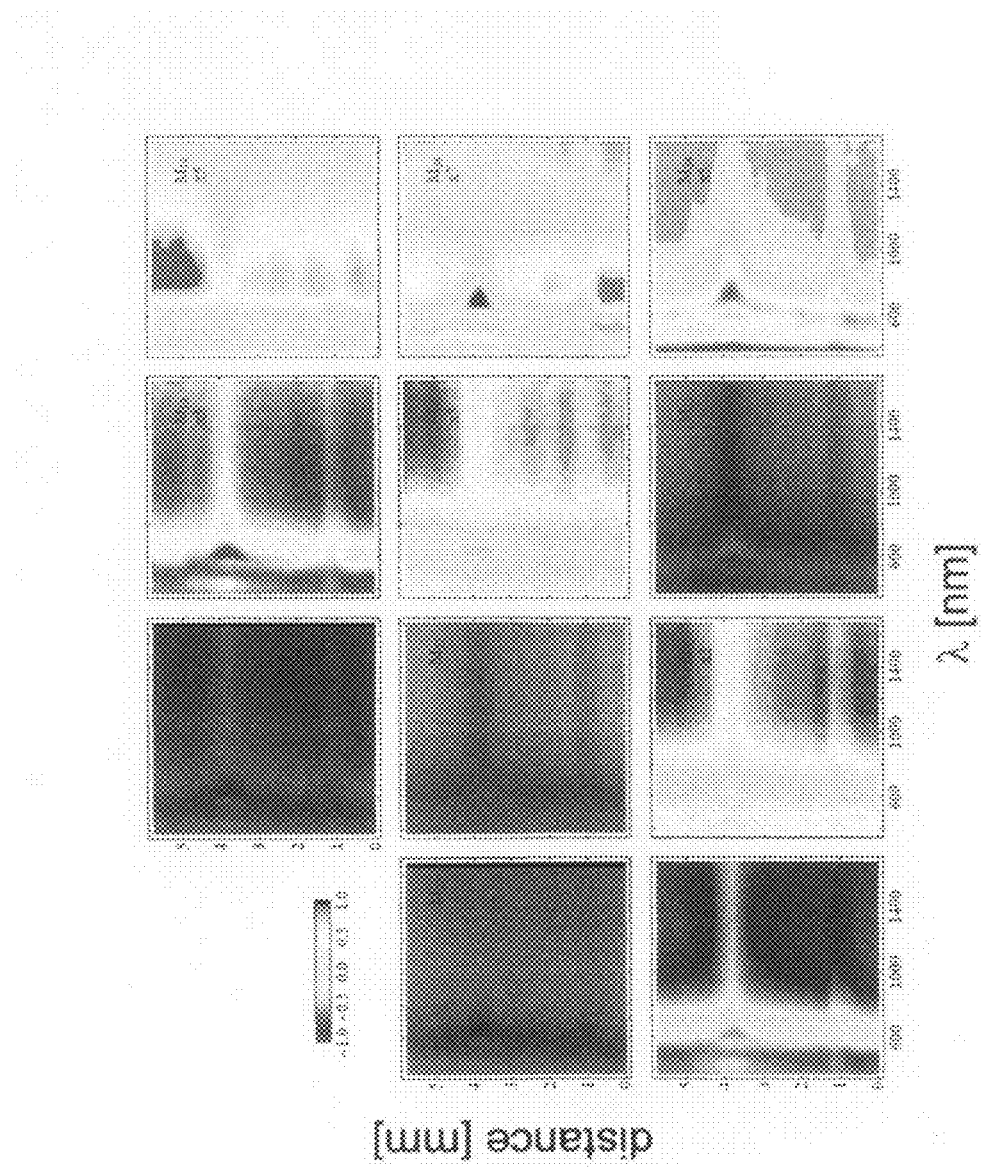
FIG. 6b show elements of a Mueller Matrix for spectroscopic data taken along line over an anisotropic sample surface at a given angle of incidence, for a line having dimensions of about 100 by 300 micrometers on a sample surface characterized by the presence of nano-fibers, each of which projects at a non-normal angle to said surface.

FIG. 6b show elements of a Mueller Matrix for spectroscopic data taken along line over an anisotropic sample surface at a given angle of incidence. Represented are spectroscopic Mueller Matrix line images for a line having dimensions of about 100 by 300 micrometers on a sample surface characterized by the presence of nano-fibers, each of which projects at a non-normal angle to said surface. The images were taken along the direction of the sample surface in which a certain dye solution was transported through a solvent that was also present. The different spectral variations along the line scan reflect the locations of different dyes along the line scan that have separated based upon their transport properties in the solvent.

Figure 7:
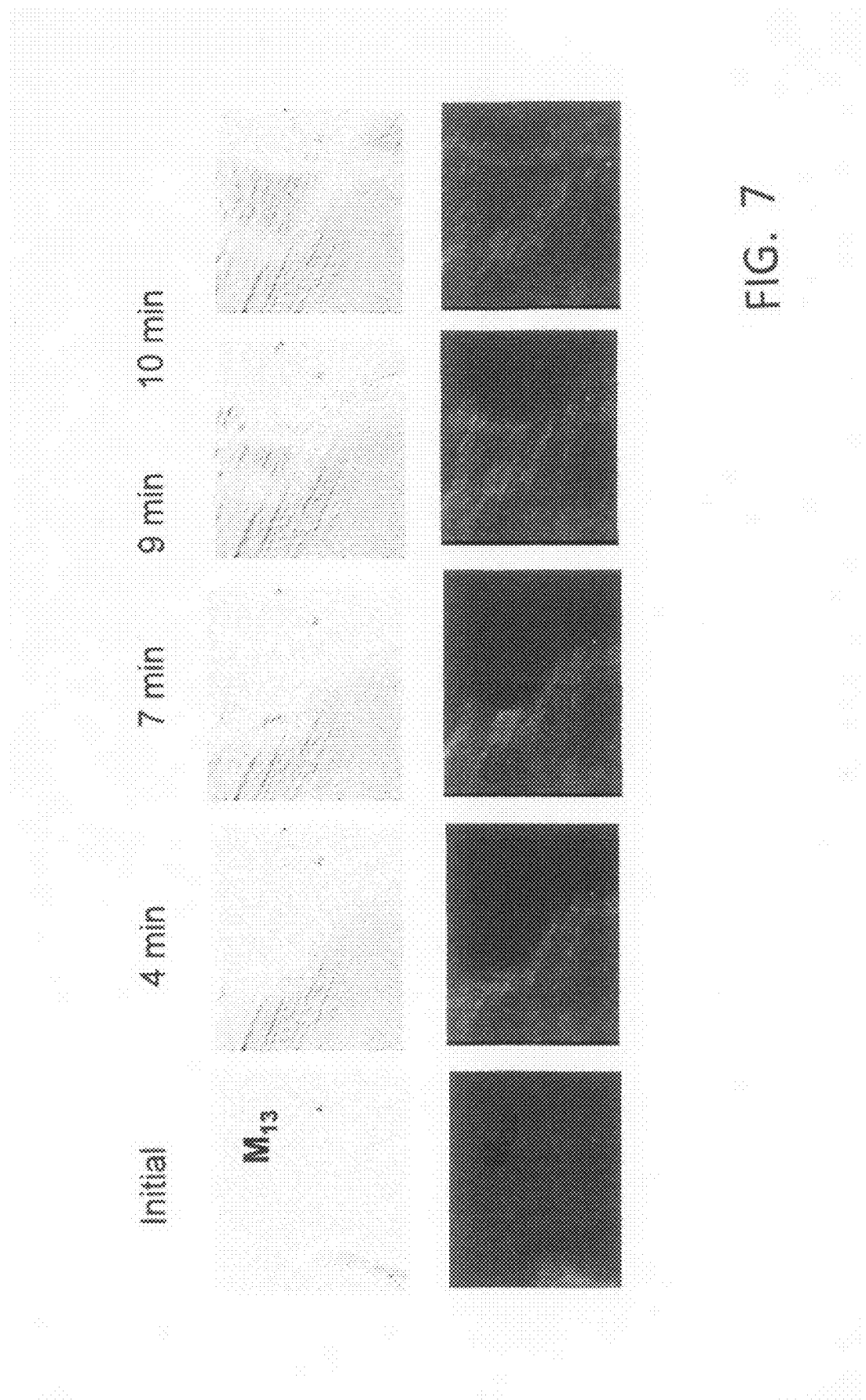
FIG. 7 demonstrates images of Mueller Matrix elements M13 and M33 for a sample at various times during solvent evaporation.

FIG. 7 demonstrates images of Mueller Matrix elements M11 (upper) and M33 (lower) for a sample at various times, (ie. 4, 7, 9 and 10 minutes) during evaporation of a solvent.

Figure 8:
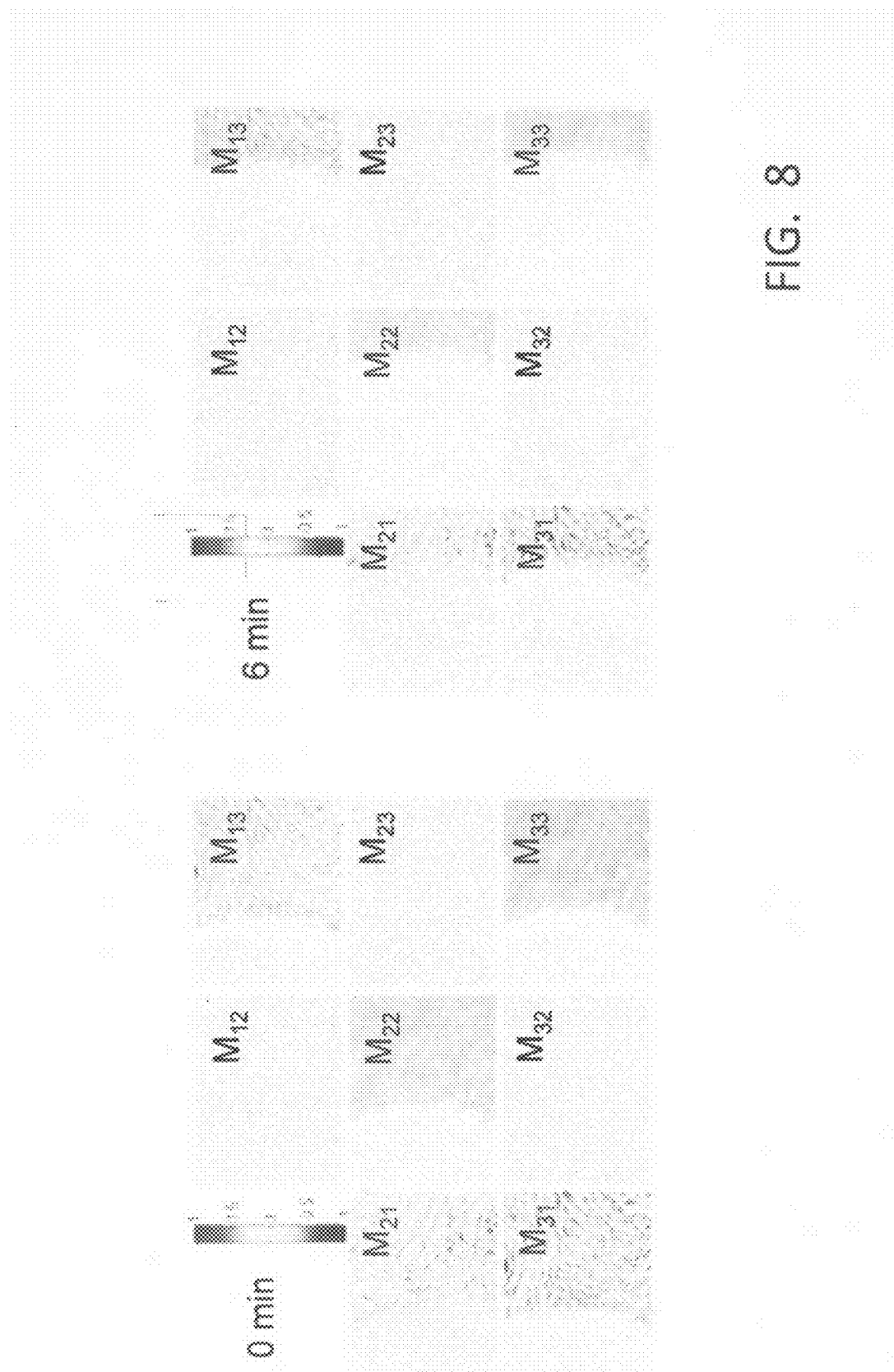
FIG. 8 demonstrates Mueller Matrix elements M12, M13, M21, M22, M23, M31, M32 and M33 for a case wherein a lipophilic test dye is transported to the right at "0" and "6" minutes.

FIG. 8 demonstrates Mueller Matrix elements M12, M13, M21, M22, M23, M31, M32 and M33 for a case wherein a lipophilic test dye is transported to the right, at "0" and "6" minutes.

The various FIGS. 5-7 are provided to demonstrate the type of results that are achievable by application of the present invention methodology. The important thing to note is how results vary from matrix Element to matrix Element, and how those results depend on the change in anisotropy of the surface, and how those results affect signals in both on and off-diagonal Mueller matrix Elements. The results occur because of the effects of Sample surfaces such as exemplified by FIGS. 3a and 3b, combined, with alignment of an electromagnetic beam, such as suggested by FIGS. 2 and 5b in reflection. In transmission, as suggested by FIG. 1, a Polarization angle can be aligned with respect to nanofiber orientation on a Sample surface, again, such as is suggested by FIGS. 3a and 3b.

Figure 9A:
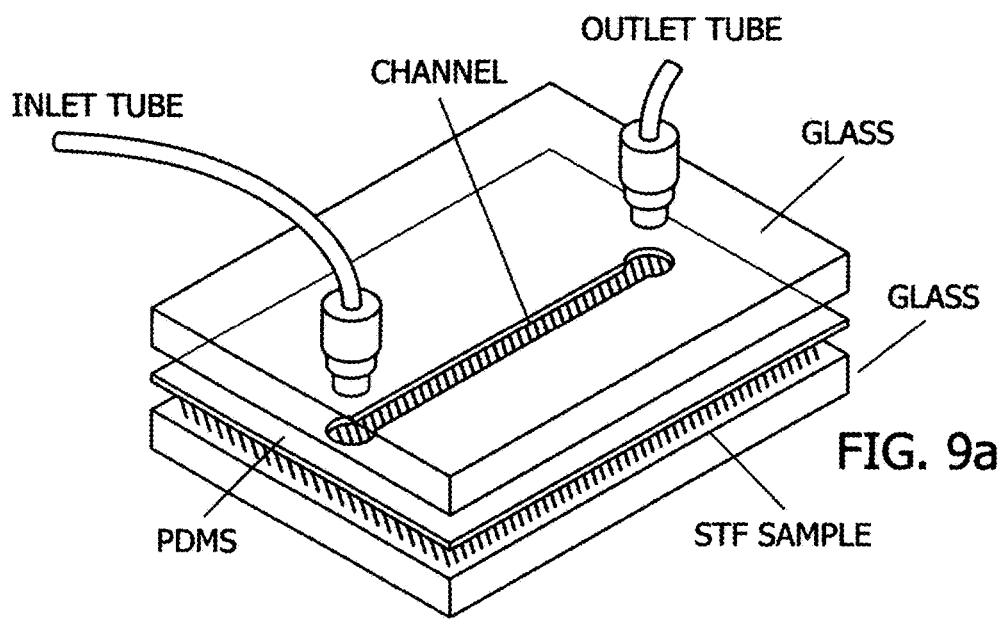
FIG. 9a shows a microchannel liquid cell with transparent top and bottom plates for application in transmission or reflection ellipsometry.

For insight to a practical apparatus that can be applied to achieve present invention results, FIG. 9a is included and shows a Microchannel (CHANNEL) liquid cell with transparent top (GLASS) and bottom (GLASS) plates. This system can be applied in both transmission or reflection ellipsometry. Note that in use Sample (STF) is flowed into the Inlet (INLET) Tube, passes through the Microchannel (CHANNEL) and exits the Output (OUTPUT) Tube. A Polymer gasket Compound (PDMS) is present to seal the Microchannel (Channel) with the Top (GLASS) and the Bottom (GLASS) Plates, and serves to define the Channel height.

Figure 9B:
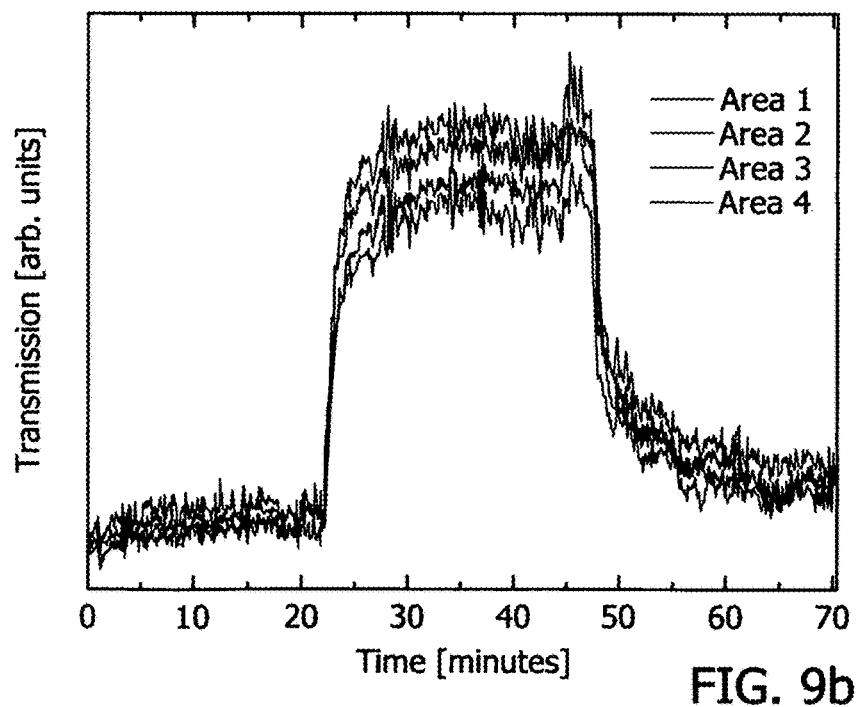
FIG. 9b shows Mueller Matrix results achieved by applying the system of FIG. 9a in transmission to a sample flowed therethrough.

FIG. 9b shows Mueller matrix results achieved by applying the system of FIG. 9a in transmission mode ellipsometry, to a sample flowed through the Microchannel (CHANNEL). At the outset (Time=0), the Microchannel has nanopure water flowing therethrough. At about 22 minutes a Target sample cetyltrimethylammonium bromide, a small molecule also known as (CTAB), is infiltrated at a concentration of 2.5 millimolar into the nanopure water. The (CTAB) molecules, which have an average length of about 2 nm, attach to the nanofibers, (see FIGS. 3a, 3b and 6aC as examples), and form a layer thereatop with a depth of about 2 nm. This causes the anisotropy of the investigated surface to change thereby leading the change in signals shown. The signals represent time-dependent combinations of Mueller matrix elements, the specifics of which need not be described here to make clear what the exemplary system in FIG. 9a enables. At about 46 minutes the microchannel (CHANNEL) is flushed with nanopure water without (CTAB) present. It is apparent that this causes the signal to approach it's original pre time=0 state.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An imaging ellipsometer or polarimeter system capable of producing at least partial Jones or Mueller matrices corresponding to a multiplicity of locations over an imaged area, comprising:
   a) a source of a beam of electromagnetic radiation;
   b) a polarization state generator;
   c) a substrate-stage comprising a multiplicity of nanostructures that project non-normal to a surface thereof; wherein the nanostructures are a chromatographic stationary phase that separates analytes;
   d) a polarization state analyzer; and
   e) a data detector;
said imaging ellipsometer or polarimeter system presenting system inherent p- and s-coordinates;
such that in use a fluid selected from the group consisting of:
   a liquid; and
   a gas;
containing one or more analytes is entered to said substrate-stage nanostructures which, over time can migrate therewithin while a beam of electromagnetic radiation from the source thereof is caused to have a polarization state imposed thereupon by the polarization state generator, then interact with said substrate-stage over an imaged area thereof, proceed through said polarization state analyzer and enter said data detector, and wherein said data detector provides output data corresponding to a multiplicity of points over said area of said substrate-stage being imaged, which output data is sufficient to enable production of said at least partial Jones or Mueller matrices that correspond to a multiplicity of locations over said imaged area.

2. An imaging ellipsometer or polarimeter system as in claim 1, wherein said substrate-stage is rotatable about a perpendicular to said surface, and wherein the beam of electromagnetic radiation approaches the surface of said substrate-stage along a substantial perpendicular thereto, then transmits therethough, passes through said polarization state analyzer, and enters said data detector, data from which can be applied to produce elements of said at least partial Jones or Mueller matrix that present with image information in diagonal or off-diagonal elements thereof, effected by rotating said substrate-stage about said perpendicular to said surface thereof to provide alignment of said nano-structures with said ellipsometer or polarimeter system p- or s-coordinates, or at a rotation angle therebetween, respectively.

3. An imaging ellipsometer or polarimeter system as in claim 1, wherein said substrate-stage is rotatable about a perpendicular to said surface, and wherein the beam of electromagnetic radiation approaches the surface of said substrate-stage non-perpendicular thereto, then transmits therethrough, passes through said polarization state analyzer, and enters said data detector, data from which can be applied to produce elements of said at least partial Jones or Mueller matrix that present with image information in diagonal or off-diagonal elements thereof by rotating said substrate-stage about said perpendicular to said surface thereof to provide alignment of said nano-structures with said ellipsometer or polarimeter system p- or s-coordinates, or at a rotation angle therebetween, respectively, and in which effects of isotropic properties of said substrate-stage are included along with anisotropic properties introduced by the presence of said nanostructures, in the data produced by the data detector, and thus appear in the elements of said at least partial Jones or Mueller matrix image information in diagonal or off-diagonal elements thereof.

4. An imaging ellipsometer or polarimeter system as in claim 1, wherein said substrate-stage is rotatable about a perpendicular to said surface, and wherein the beam of electromagnetic radiation approaches the surface of said substrate-stage along a non-perpendicular thereto such that a plane of incidence is defined, then reflects therefrom, passes through said polarization state analyzer and enters said data detector, data from which can be applied to produce elements of said at least partial Jones or Mueller matrix that present with image information in diagonal or off-diagonal elements thereof effected by rotating said substrate-stage about said perpendicular to said surface thereof, to provide alignment of said nano-structures with said ellipsometer or polarimeter system p- or s-coordinates, or at a rotation angle therebetween, respectively.

5. An imaging ellipsometer or polarimeter system as in claim 4, wherein a preferred rotation angle of said substrate-stage provides that said plane of incidence is at an angle to the direction in which said non-normal nanostructures are caused to project within said said ellipsometer or polarimeter system p- and s-coordinate system.

6. An imaging ellipsometer or polarimeter system as in claim 5 in which the preferred rotation angle of said substrate-stage provides that said plane of incidence is at an essentially 45 degree angle to the direction in which said non-normal nanostructures are caused to project within said ellipsometer or polarimeter system p- and s-coordinate system.

7. An imaging ellipsometer or polarimeter system as in claim 1, wherein the non-normal nanostructures of said substrate-stage are formed by glancing angle deposition thereof onto said surface.

8. An imaging ellipsometer or polarimeter system as in claim 1, wherein the source of electromagnetic radiation provides wavelengths in a THZ to UV spectral range.

9. An imaging ellipsometer or polarimeter system as in claim 1, wherein the polarization state generator and polarization state analyzer are each fixed polarizers, before and after the substrate-stage, respectively, and in which each said fixed polarizer can be aligned relative to nanostructure orientation such that data detector sensitivity to anisotropic properties of said nanostructures is enhanced.

10. An imaging ellipsometer or polarimeter system as in claim 9, in which the two fixed polarizers are crossed, so as to enable detection of Jones or Mueller matrix off-diagonal elements that provide insight to said anisotropic properties.

11. An imaging ellipsometer or polarimeter system as in claim 1 in which said substrate-stage is contained within a substantially enclosed cell which comprises windows through which said beam of electromagnetic radiation enters and exits.

12. An imaging ellipsometer or polarimeter system as in claim 11 in which said windows are oriented so that said beam of electromagnetic radiation enters and exits perpendicular thereto.

13. An imaging ellipsometer or polarimeter system as in claim 1 in which the substrate-stage is oriented such that said beam of electromagnetic radiation directly encounters said nanostructures.

14. An imaging ellipsometer or polarimeter system as in claim 1 in which the substrate-stage is oriented such that said beam of electromagnetic radiation passes through the surface before encountering said nanostructures.

15. An imaging ellipsometer or polarimeter system as in claim 1 in which said beam of electromagnetic radiation is caused to approach the substrate-stage along a substantial perpendicular to the surface thereof, while the nanostructures are oriented to project in a desired direction, such that the p- and s-coordinates of said imaging ellipsometer or polarimeter system can be calibrated thereto.

16. An imaging ellipsometer or polarimeter system as in claim 1, in which the fluid contains one or more analytes, and in which sensitivity to anisotropic properties of said nanostructures is enhanced in their vicinity.

17. An imaging ellipsometer or polarimeter system as in claim 1 in which said multiplicity of nano-structures that project non-normal to is substantially planar.

18. An imaging ellipsometer or polarimeter system as in claim 1 in which said multiplicity of nano-structures that project non-normal to is other than substantially planar.

19. A method of monitoring an interaction of a fluid with a substrate comprising the steps of:
   a) providing a system that is an imaging ellipsometer or polarimeter capable of determining and imaging elements of an at least partial Jones, or at least partial Mueller matrix for each of a multiplicity of positions over an imaged area of a substrate;
   b) providing a substrate that comprises nanostructures that project from a substantially planar substrate surface non-normal thereto; wherein the nanostructures are a chromatographic stationary phase that separates analytes;
   c) entering a fluid selected from the group consisting of:
      a liquid, and
      a gas;
   to said substrate nanostructures;
   d) applying said provided system to determine and provide an observable image that provides insight to anisotropic properties of said substrate-fluid combination for at least one element of said determined at least partial Jones or Mueller matrix corresponding to said imaged area of said substrate.

20. A method as in claim 19, in which the provided system comprises a source of electromagnetic radiation that provides wavelengths in a THZ to UV spectral range.

21. A method as in claim 19, wherein the non-normal nanostructures of said substrate are formed by glancing angle deposition thereof onto said surface.

22. A method as in claim 19 wherein the anisotropic properties of said substrate-fluid combination for at least one element of said determined at least partial Jones or Mueller matrix corresponding to said imaged area of said substrate is determined by obtaining multiple data sets that correspond to multiple orientations of said substrate-fluid combination and performing a simultaneous regression thereonto to provide information regarding anisotropy.

23. A method as in claim 19 wherein the anisotropic properties of said substrate-fluid combination for at least one element of said determined at least partial Jones or Mueller matrix corresponding to said imaged area of said substrate is determined and observed over time to capture dynamics of a process.

24. A method as in claim 19 wherein properties of said substrate for at least one element of said determined at least partial Jones or Mueller matrix corresponding to said imaged area of said substrate is determined in a first step, followed by introduction of the fluid to said nanostructures and the anisotropic properties of said substrate-fluid combination for at least one element of said determined at least partial Jones or Mueller matrix corresponding to said imaged area of said substrate is then determined in a second step.

25. A method as in claim 24 wherein a difference between results obtained in said first and second steps is analyzed.

26. A method as in claim 19 in which results determined are applied to determine analyte type present in said fluid.

27. A method as in claim 19 wherein results determined provide insight into travel and separation of analyte constituents over a period of time after the containing fluid is entered to said nanostructures.

28. A method as in claim 19 wherein results determined provide insight into travel and separation of analyte constituents over a period of time after the containing fluid is entered to said nanostructures and therefore strength of interaction.

29. A method as in claim 19 wherein results determined provide insight into volume within the nanostructures.

30. A method as in claim 19 wherein results determined provide real time results.

31. A method as in claim 19 wherein nanostructure geometry is engineered to emphasise nano-fluidic properties of the nanostructures in relation to their shape.

32. A method as in claim 19 wherein nanostructure geometry is engineered to create an anisotropic solvent flow profile.

33. A method as in claim 19 wherein nanostructure geometry is engineered to create solvent flow profiles in one, two or three dimensions.

34. A method as in claim 19, in which the provided imaging ellipsometer or polarimeter comprises:
   a) a source of a beam of electromagnetic radiation;
   b) a polarization state generator;
   c) a substrate-stage comprising the nanostructures that project non-normal to the surface thereof, said substrate-stage being rotatable about a perpendicular to said surface;
   d) a polarization state analyzer; and
   e) a data detector;
said imaging ellipsometer or polarimeter system presenting inherent p- and s-coordinates;
such that in use a fluid selected from the group consisting of:
   a liquid; and
   a gas;
containing one or more analytes is entered to said substrate-stage nanostructures which, over time can migrate therewithin while a beam of electromagnetic radiation from the source thereof is caused to have a polarization state imposed thereupon by the polarization state generator, then interact with said substrate-stage over an imaged area thereof, proceed through said polarization state analyzer and enter said data detector, and wherein said data detector provides output data corresponding to a multiplicity of points over said area of said substrate-stage being imaged, which output data is sufficient to enable production of said at least partial Jones or Mueller matrices that correspond to a multiplicity of locations over said imaged area.

35. A method as in claim 34, wherein the beam of electromagnetic radiation is directed to approach the surface of said substrate along a substantial perpendicular thereto, then transmits therethough, passes through said polarization state analyzer, and enters said data detector, data from which can be applied to produce elements of said at least partial Jones or Mueller matrix that present with image information in diagonal or off-diagonal elements thereof effected by rotating said substrate about said perpendicular to said surface thereof to provide alignment of said nano-structures with said ellipsometer or polarimeter system p- or s-coordinates, or at a rotation angle therebetween, respectively.

36. A method as in claim 34, wherein the beam of electromagnetic radiation is directed to approach the surface of said substrate non-perpendicular thereto, then transmits therethrough, passes through said polarization state analyzer, and enters said data detector, data from which can be applied to produce elements of said at least partial Jones or Mueller matrix that present with image information in diagonal or off-diagonal elements thereof by rotating said substrate about said perpendicular to said surface thereof to provide alignment of said nano-structures with said ellipsometer or polarimeter system p- or s-coordinates, or at a rotation angle therebetween, respectively, and in which effects of isotropic properties of said substrate are included along with anisotropic properties introduced by the presence of said nanostructures, in the data produced by the data detector, and thus appear in the elements of said at least partial Jones or Mueller matrix image information in diagonal or off-diagonal elements thereof.

37. An method as in claim 34, wherein the beam of electromagnetic radiation is directed to approach the surface of said substrate along a non-perpendicular thereto such that a plane of incidence is defined, then reflects therefrom, passes through said polarization state analyzer and enters said data detector, data from which can be applied to produce elements of said at least partial Jones or Mueller matrix that present with image information in diagonal or off-diagonal elements thereof effected by rotating said substrate about said perpendicular to said surface thereof, to provide alignment of said nano-structures with said ellipsometer or polarimeter system p- or s-coordinates, or at a rotation angle therebetween, respectively.

38. A method as in claim 37, wherein a preferred rotation angle of said substrate provides that said plane of incidence is at an angle to the direction in which said non-normal nanostructures are caused to project within said said ellipsometer or polarimeter system p- and s-coordinate system.

39. A method as in claim 21, in which the preferred rotation angle of said substrate-stage provides that said plane of incidence is at an essentially 45 degree angle to the direction in which said non-normal nanostructures are caused to project within said ellipsometer or polarimeter system p- and s-coordinate system.

40. A method system as in claim 34, in which the fluid contains one or more analytes, and in which sensitivity to anisotropic properties of said nanostructures is enhanced in their vicinity.

41. A method as in claim 34, wherein the polarization state generator and polarizations state analyzer are each fixed polarizers, before and after the substrate, respectively, and in which each said fixed polarizer can be aligned relative to nanostructure orientation such that data detector sensitivity to anisotropic properties of a fluid entered into said nanostructures is enhanced.

42. A method as in claim 41, in which the two fixed polarizers are crossed, so as to enable detection of Jones or Mueller matrix off-diagonal elements that provide insight to said anisotropic properties.

43. A method as in claim 34 in which said substrate is contained within a substantially enclosed cell which comprises windows through which said beam of electromagnetic radiation enters and exits.

44. A method as in claim 43 in which said windows are oriented so that said beam of electromagnetic radiation enters and exits perpendicular thereto.

45. A method as in claim 34 in which the substrate is oriented such that said beam of electromagnetic radiation directly encounters said nanostructures.

46. A method as in claim 34 in which the substrate is oriented such that said beam of electromagnetic radiation passes through the surface before encountering said nanostructures.

47. A method as in claim 34 in which said beam of electromagnetic radiation is caused to approach the substrate along a substantial perpendicular to the surface thereof, while the nanostructures are oriented to project in a desired direction, such that the p- and s-coordinates of said imaging ellipsometer or polarimeter system can be calibrated thereto.

* * * * *